(12) United States Patent
Marsh et al.

(10) Patent No.: US 10,220,154 B2
(45) Date of Patent: Mar. 5, 2019

(54) DRUG DELIVERY DEVICE

(71) Applicant: Sanofi, Paris (FR)

(72) Inventors: William Marsh, Buckinghamshire (GB); Anthony Paul Morris, Coventry West Midlands (GB); Joseph Butler, Rugby (GB); Matthew Jones, Warwick (GB); Samuel Steel, Warwickshire (GB); Richard James Vincent Avery, Gloucestershire (GB)

(73) Assignee: Sanofi, Paris (FR)

( * ) Notice: Subject to any disclaimer, the term of this patent is extended or adjusted under 35 U.S.C. 154(b) by 69 days.

(21) Appl. No.: 15/321,900

(22) PCT Filed: Jul. 1, 2015

(86) PCT No.: PCT/EP2015/064986
§ 371 (c)(1),
(2) Date: Dec. 23, 2016

(87) PCT Pub. No.: WO2016/001306
PCT Pub. Date: Jan. 7, 2016

(65) Prior Publication Data
US 2017/0136186 A1 May 18, 2017

(30) Foreign Application Priority Data
Jul. 1, 2014 (EP) ..................... 14306067

(51) Int. Cl.
*A61M 5/315* (2006.01)
*A61M 5/20* (2006.01)
*A61M 5/31* (2006.01)

(52) U.S. Cl.
CPC ............ *A61M 5/3157* (2013.01); *A61M 5/20* (2013.01); *A61M 5/2033* (2013.01);
(Continued)

(58) Field of Classification Search
CPC ............ A61M 5/31541; A61M 5/3155; A61M 5/3157; A61M 5/31593; A61M 5/31533;
(Continued)

(56) References Cited

U.S. PATENT DOCUMENTS

2009/0275914 A1* 11/2009 Harms ..................... A61M 5/24
604/506

FOREIGN PATENT DOCUMENTS

| WO | WO 2006/076921 | 7/2006 |
| WO | WO 2006/079481 | 8/2006 |

(Continued)

OTHER PUBLICATIONS

International Search Report and Written Opinion in International Application No. PCT/EP2015/064986, dated Oct. 1, 2015, 11 pages.
(Continued)

*Primary Examiner* — Deanna K Hall
(74) *Attorney, Agent, or Firm* — Fish & Richardson P.C.

(57) ABSTRACT

The present disclosure is generally directed to a drug delivery device for selecting and dispensing a number of user variable doses of a medicament. The device comprises a housing (10), a dose selector (80) operable to set a dose by rotation relative to the housing (10), a number sleeve (60) arranged within the housing (10) such that at least a portion of the number sleeve (60) is visible through a first aperture (11b) in the housing (10), a piston rod (30) coupled to the housing (10) and to a drive sleeve (40) such that rotation of the drive sleeve (40) relative to the housing (10) causes the piston rod (30) to translate relative to the housing (10) and a clutch mechanism arranged between the number sleeve (60) and the drive sleeve (40). The clutch mechanism comprises a first interface (42, 62) for rotationally constraining the drive sleeve (40) and the number sleeve (60) depending on the axial position of the drive sleeve (40) and a second
(Continued)

interface (43, 121) for rotationally constraining the drive sleeve (40) and the number sleeve (60) via a clutch element (120) depending on the axial position of the drive sleeve (40) and/or the bias of a clutch spring (130).

16 Claims, 8 Drawing Sheets

(52) U.S. Cl.
CPC .... *A61M 5/31515* (2013.01); *A61M 5/31541* (2013.01); *A61M 5/31551* (2013.01); *A61M 5/31553* (2013.01); *A61M 5/31583* (2013.01); *A61M 5/31585* (2013.01); *A61M 5/3146* (2013.01); *A61M 5/31511* (2013.01); *A61M 2005/3126* (2013.01); *A61M 2205/581* (2013.01); *A61M 2205/582* (2013.01); *A61M 2205/585* (2013.01)

(58) Field of Classification Search
CPC .......... A61M 5/31576; A61M 5/31578; A61M 5/31585
USPC .................................................. 604/207, 211
See application file for complete search history.

(56) References Cited

FOREIGN PATENT DOCUMENTS

| | | |
|---|---|---|
| WO | WO 2010/149209 | 12/2010 |
| WO | WO 2011/060785 | 5/2011 |
| WO | WO 2012/125876 | 9/2012 |
| WO | WO 2014/033197 | 3/2014 |

OTHER PUBLICATIONS

International Preliminary Report on Patentability in International Application No. PCT/EP2015/064986, dated Jan. 3, 2017, 8 pages.

* cited by examiner

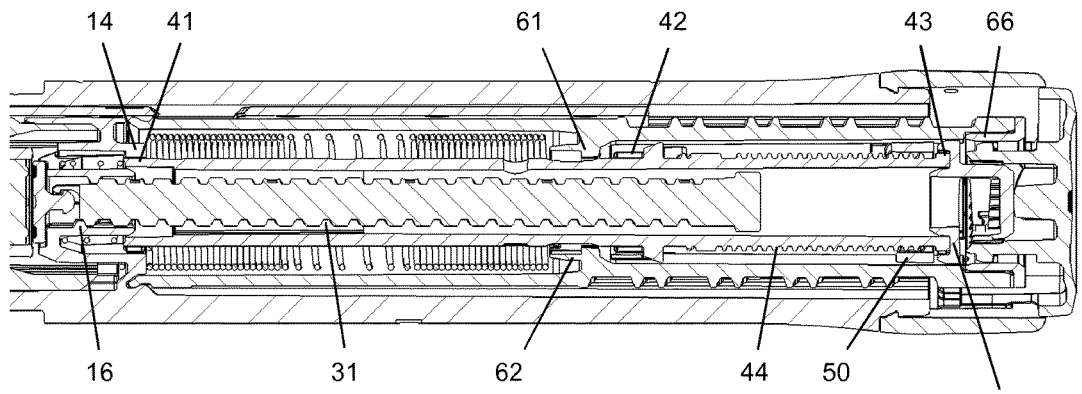
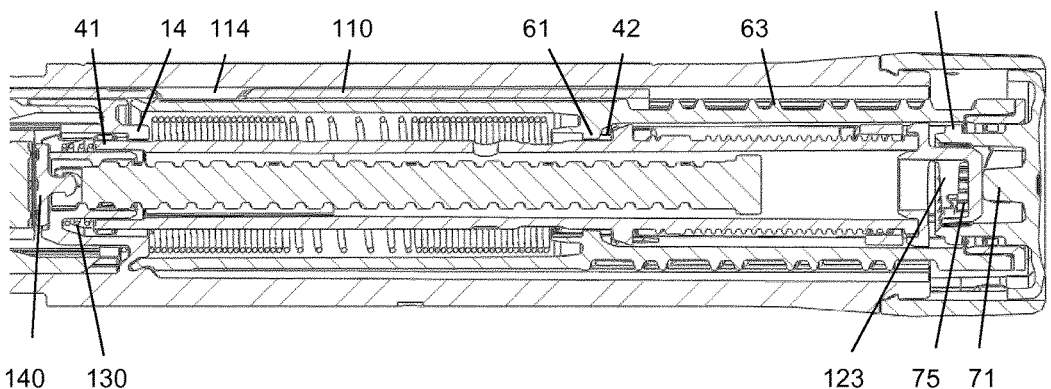
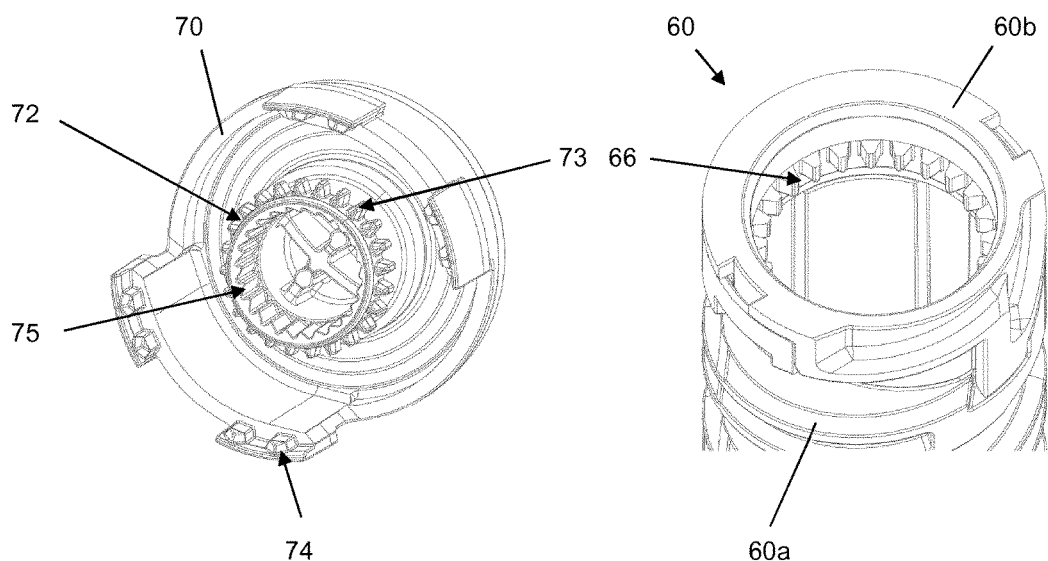

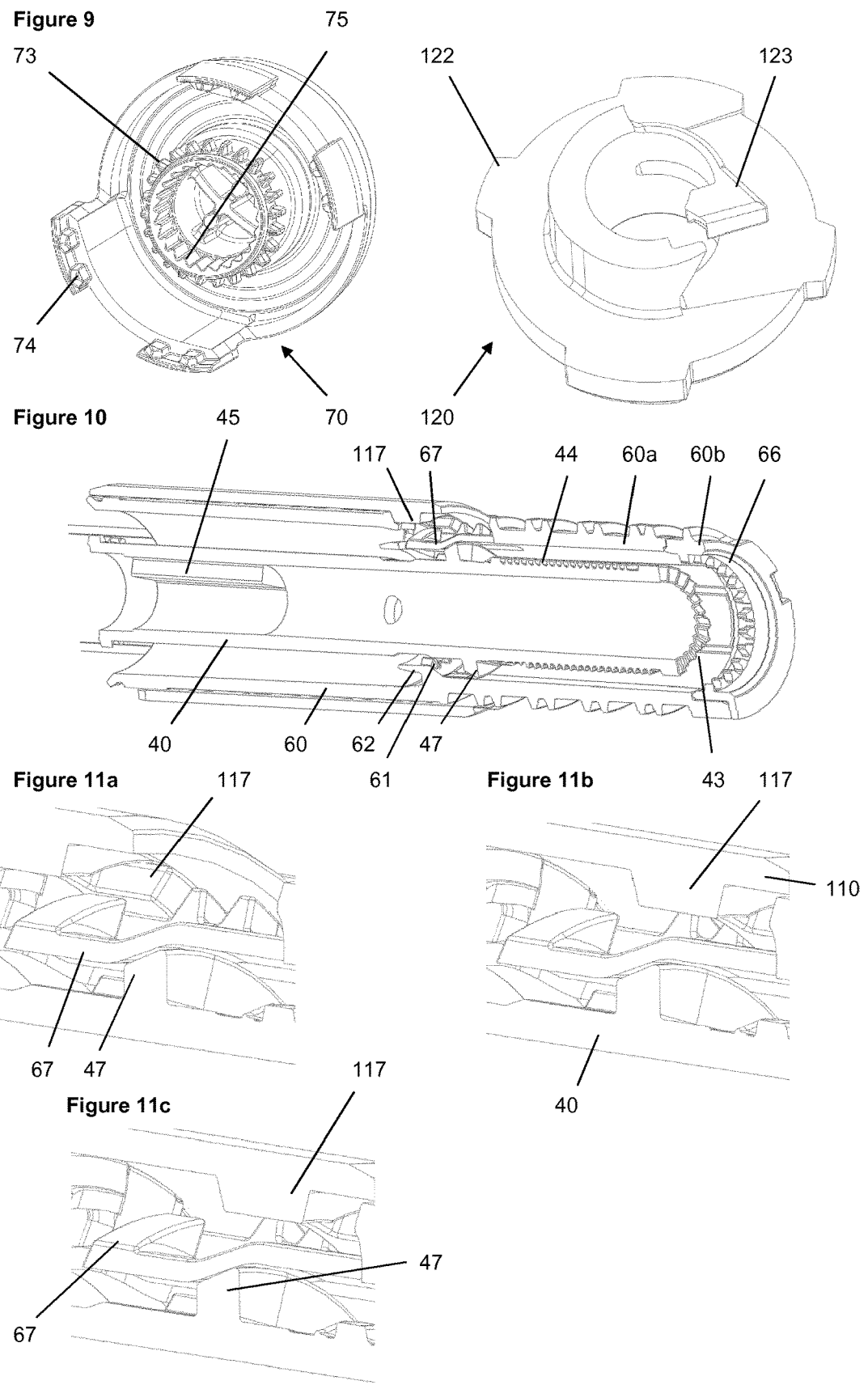

Figure 21
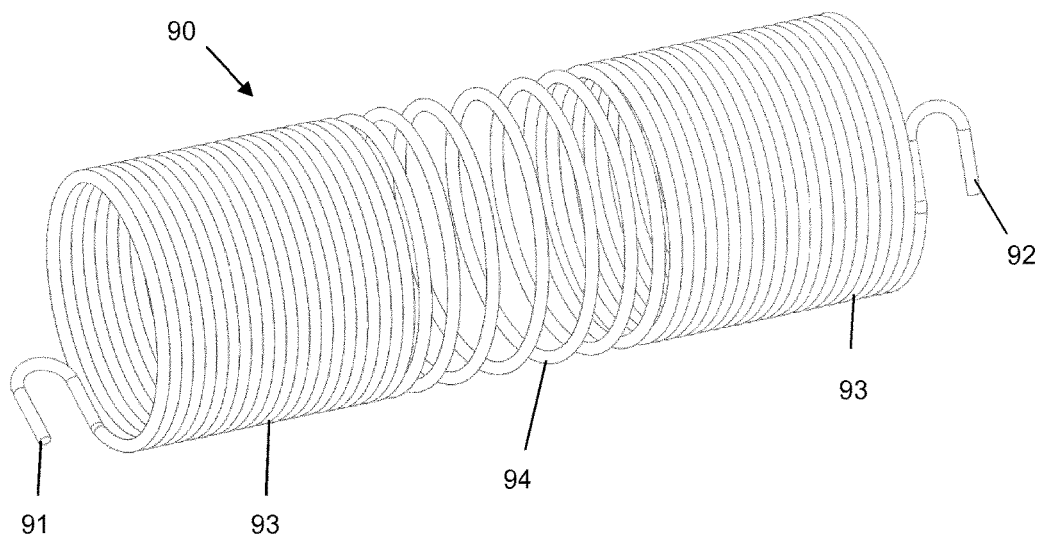
Figure 22a        Figure 22b        Figure 22c
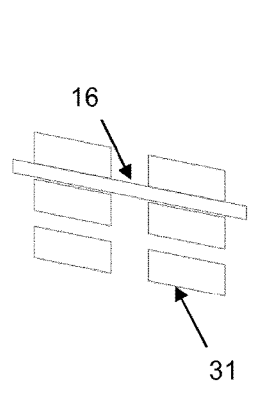 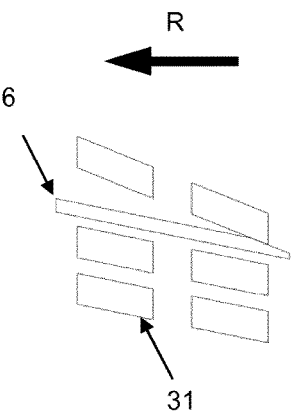 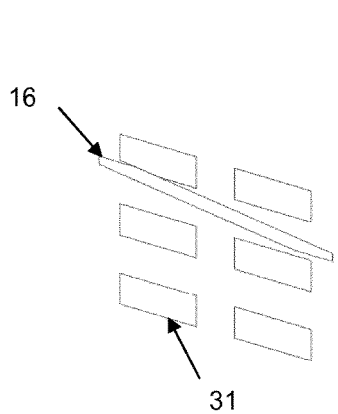

DRUG DELIVERY DEVICE

CROSS-REFERENCE TO RELATED APPLICATIONS

This application is a U.S. national stage application under 35 USC § 371 of International Application No. PCT/EP2015/064986, filed on Jul. 1, 2015, which claims priority to European Patent Application No. 14306067.1 filed on Jul. 1, 2014, the entire contents of which are incorporated herein by reference.

The present disclosure is generally directed to a drug delivery device suitable for selecting and dispensing a number of user variable doses of a medicament.

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so-called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for both types of devices, i.e. for disposable devices as well as for reusable devices.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

WO 2014/033197 A1 describes a manually driven drug delivery device with a housing, a dose setting button operable to set a dose by rotation relative to the housing, a number sleeve arranged within the housing such that at least a portion of the number sleeve is visible through a first aperture in the housing, a piston rod coupled to the housing and to a driver such that rotation of the driver relative to the housing causes the piston rod to translate relative to the housing, and a clutch mechanism releasably coupling the number sleeve and the driver. The driver is permanently rotationally locked to the dose setting button which is releasably coupled to the number sleeve such that the driver, the dose setting button and the number sleeve are rotationally constrained during dose setting. During dose dispensing the driver and the dose setting button are rotationally constrained to the housing and the number sleeve is allowed to rotate relative to the driver and the dose setting button.

In some cases the clutch mechanism between the number sleeve and the driver has to transmit relatively high forces or torques. If this clutch mechanism would fail, e.g. due to an overload, the whole drug delivery device is unusable.

Certain implementations of the subject matter described in this disclosure can be implemented to provide an improved drug delivery device having an increased reliability.

Certain implementations of the subject matter described in this disclosure can be implemented as a drug delivery device according to claim 1. According to the invention the clutch mechanism comprises two separate ways of coupling the drive sleeve and the number sleeve. Thus, even if one of the couplings were damaged or were to slip, the device could still be used transmitting torque via the other coupling. For example, the clutch mechanism comprises a first interface for rotationally constraining the drive sleeve and the number sleeve depending on the axial position of the drive sleeve and a second interface for rotationally constraining the drive sleeve and the number sleeve via a clutch element, preferably again depending on the axial position of the drive sleeve and/or the bias of a clutch spring. Preferably, both interfaces rotationally constrain the drive sleeve and the number sleeve during dose dispensing, while allowing relative rotation during dose setting.

According to a first embodiment of the present disclosure the drive sleeve is axially movable between a first, proximal dose setting or dose correction position and a second, distal dose dispensing position. In other words, the axial position of the drive sleeve, e.g. with respect to the housing and/or the number sleeve, determines the state of the drug delivery device, namely either the dose setting or dose correction mode or the dose dispensing mode. Dose correction is understood to be reducing an already set dose without dispensing medicament.

The axial movement of the drive sleeve may either simultaneously result in engagement or disengagement of both interfaces or may result in an engagement of the interfaces one after the other e.g. depending on the degree of axial displacement of the drive sleeve. For example, one of the interfaces may be permanently in engagement either in a mode allowing slipping (overhauling) of the interface or upon axial displacement of the drive sleeve in a mode preventing slipping of the interface.

Preferably, the first interface comprises splines on the outer surface of the drive sleeve and corresponding splines or grooves on the inner surface of the number sleeve. The splines or grooves are arranged such that in a first axial position, which is for example the dose dispensing position, of the drive sleeve relative to the housing and/or the number sleeve the splines or grooves are engaged rotationally constraining the drive sleeve to the number sleeve. Further, in a second axial position, which is for example the dose setting or correcting position, of the drive sleeve relative to the housing and/or the number sleeve the splines or grooves are disengaged allowing relative rotation of the drive sleeve and the number sleeve.

The second interface may comprise ratchet clutch features on the drive sleeve adapted to engage corresponding ratchet clutch features on the clutch element which in turn is rotationally permanently constrained to the number sleeve. The ratchet clutch features preferably allow movement in both directions during dialing (so it acts like a detent), but no movement during dispense (so it acts a clutch). This ratchet may have various functions. In addition to rotationally constraining the drive sleeve and the number sleeve during dose dispensing, the ratchet clutch features may be permanently in contact, i.e. also during dose setting or dose correction, producing a feedback signal upon relative rotation of the drive sleeve and the number sleeve. Preferably, the ratchet clutch features and the corresponding ratchet clutch features comprise teeth having a ramp angle allowing overhauling of each other for dose correction. Further, this ratchet clutch interface may be designed, e.g. by providing meshing ratchet teeth on the drive sleeve and on the clutch element, such that relative rotation of the drive sleeve and the number sleeve requires relatively low force or torque in one direction, preferably the dose setting direction, and requires a significantly higher force or torque in the opposite direction, preferably the dose correction direction. For example, in the dose setting direction, a shallow ramp reduces the torque but winding up the spring increases the torque, while in the dose correction direction, a steep ramp increases the torque but unwinding the spring reduces the torque. Thus, the torque for dose correction and dose dialing may therefore be equal, but one may be larger than the other. As an alternative, the ratchet features may be designed to allow relative rotation of the drive sleeve and the number sleeve only in one direction, typically the dose setting direction, while fully preventing relative rotation of the drive sleeve and the number sleeve only in the opposite direction.

For example, the ratchet clutch features may each comprise a series of teeth, preferably saw-teeth, which are allowed to slip over each other if not pressed against each other too firmly. In other words, the clutch features may be overhauled against the bias of the clutch spring by allowing the drive sleeve and/or the clutch element to translate axially against the force of the clutch spring. This may result in an oscillating axial movement of the drive sleeve and/or the clutch element due to continued disengagement and following re-engagement into the next detented position. An audible click may be generated by this re-engagement, and tactile feedback may be given by the change in torque input required.

Preferably, the second interface provides a detented position between the drive sleeve and the clutch element corresponding to each dose unit, and engages different ramped tooth angles during clockwise and anti-clockwise relative rotation. This is especially useful if the device further comprises a drive spring having a force or torque which is reacted via the second interface from the clutch element and the drive sleeve to the housing. The drive spring may be directly or indirectly coupled to the clutch element.

Temporary or permanent engagement of the second interface may be achieved by the clutch spring which is preferably located axially interposed between the housing and the drive sleeve. The clutch spring may bias the drive sleeve towards the clutch element. Overhauling or slipping of the second interface may require an axial displacement of the drive sleeve and/or the clutch element against the bias of the clutch spring.

The clutch spring may be a compression spring, preferably an axially acting compression spring. As an alternative, the clutch spring may be a pull spring. In a preferred embodiment the clutch spring is a coil spring. As an alternative, the clutch spring may be a spring washer or a block or sleeve made from an elastically deformable material like rubber. Although the clutch spring is referred to herein as a single spring, the disclosure encompasses embodiments of the clutch spring comprising more than one single spring element, which spring elements may be arranged in parallel or in series.

The second interface may be arranged such that the ratchet clutch features are rotationally constrained when the drive sleeve is in the distal position with the clutch spring being compressed to a state not allowing further axial displacement of the drive sleeve, at least not to a degree which is required for overhauling the ratchet clutch features.

In a further embodiment of the present disclosure the drive sleeve comprises a further (third) interface for permanently rotationally constraining the drive sleeve and the piston rod. For example, this third interface may comprise one or more splines or grooves on the drive sleeve inner surface and the piston rod outer surface which are in permanent engagement. If the piston rod or lead screw is in threaded engagement with the housing, rotation of the drive sleeve during dose dispensing results in advancing the piston rod relative to the housing. As an alternative, the piston rod may be splined to the housing and threaded to the drive sleeve.

The drive sleeve may comprise a further (fourth) interface for rotationally constraining the drive sleeve and the housing depending on the axial position of the drive sleeve. For example, this fourth interface may comprise one or more splines or grooves on the drive sleeve outer surface and an inner surface of the housing. Axial displacement of the drive sleeve engages or disengages the splines or grooves. Preferably, the length and position of these splines or grooves is such that the splines of the first interface engage shortly before disengagement of the fourth interface. In other words, the first and fourth interfaces are designed and arranged such that actuation e.g. of a button rotationally constrains the drive sleeve to the number sleeve before the drive sleeve is allowed to rotate relative to housing. Similarly, as the button is released after dose dispensing axial movement of the drive sleeve first rotationally constrains the drive sleeve to the housing and thereafter decouples splines of the first interface.

The drive sleeve is preferably coupled to a button via the clutch element, e.g. such that upon actuation of the button the drive sleeve and the clutch element are translated against the bias of the clutch spring from a proximal position in which the drive sleeve is rotationally locked to the housing into a distal position in which the drive sleeve is rotationally un-locked from the housing. Upon release of the button the clutch spring may translate the drive sleeve, the clutch element and the button into the proximal position. In other words, actuation of the button causes displacement of the drive sleeve and, thus, switching between the dose setting mode and the dose dispensing mode of the device.

The drug delivery device may comprise at least one clicker arrangement for generating an audible and/or tactile feedback signal during dose setting, during dose dispensing and/or at the end of dose dispensing.

For example, the drive sleeve may comprise an additional (fifth) interface for generating a feedback signal upon rotation of the drive sleeve and depending on the axial position of the drive sleeve. This signal may be an end of dose dispensing indication. In other words, the clicker arrangement may be activated to generate the feedback signal by bringing the drive sleeve in its dose dispensing position and may be de-activated preventing generation of a signal by bringing the drive sleeve in its dose setting position. This allows the feedback signal to be produced only in a defined mode. Thus, during storage or dialing the clicker arm is not deflected and will not suffer creep deformation. In addition the clicker arrangement does not cause friction losses during dialing or dose correction which contributes to a user-friendly device requiring only low dialing force or torque.

The feedback signal generated by the clicker arrangement is preferably distinct from other signals which may be generated in a drug delivery device, for example a visual indication and/or an audible and/or tactile feedback signal generated during dose setting, dose correction and/or dose dispensing.

Preferably, the drug delivery device comprises a clicker arrangement having a clicker arm on the number sleeve, a ramp on the drive sleeve and a cam on a further element, for example a gauge element, wherein upon relative rotation of the number sleeve and the gauge element the clicker arm is elastically deflectable by the cam and relaxable upon disengagement with the cam thereby generating an audible and/or tactile feedback signal. When the drive sleeve is in a first axial position, the ramp preferably does not interact with the clicker arm and, thus, the clicker arm does not contact the cam, and when the drive sleeve is in a second axial position, the ramp deflects the clicker arm such that the clicker arm contacts the cam. The number sleeve and the gauge element may be in threaded engagement. Thus, the gauge element is axially displaced upon relative rotation of the number sleeve. This allows engagement and dis-engagement of the cam and the clicker arm depending on the relative axial position of the cam and the clicker arm.

Preferably, the element comprising the clicker arm, e.g. the number sleeve, is a tubular element with the clicker arm being deflectable radially inwards and outwards. The drive sleeve comprising the ramp is preferably arranged radially inwards of the element comprising the clicker arm such that the ramp is able to push the clicker arm radially outwards. The element comprising the cam, e.g. the gauge element, may be arranged radially outwards of the element comprising the clicker arm such that the cam is able to push the clicker arm radially inwards.

There are various ways of generating the audible and/or tactile feedback signal by any of the clicker arrangements of the present disclosure. For example, the audible and/or tactile feedback signal may be generated by disengagement of a clicker arm and a tooth or a cam. In other words, the signal is caused e.g. by the pre-tensioned clicker arm falling off an edge of the tooth or cam. As an alternative, the audible and/or tactile feedback signal may be generated by contact of a first portion of the clicker arm with the tooth or cam after disengagement of a second portion of the clicker arm with the tooth or cam. For example, the second portion of the clicker arm, e.g. a crank portion, may hit the tooth or cam after the first portion of the clicker arm, e.g. a projecting tip of the arm, disengages or loses contact with the tooth or cam. In an embodiment comprising a cam it is preferred if the element with the cam further comprises a recess for receiving the second portion, e.g. the tip, of the clicker arm after disengagement of the second portion of the clicker arm with the cam.

According to a further embodiment, the drug delivery device comprises a drive spring. Preferably, relative rotation of the number sleeve and the drive sleeve during dose setting strains the drive spring and the drive spring is allowed to relax during dose dispensing thereby rotationally driving the number sleeve, the drive sleeve and the piston rod.

In a preferred embodiment, the drive spring is a torsion spring rotationally coupled to the clutch element. The drive spring may be prestrained and/or may be strained (charged) by relative rotation between drive sleeve and clutch element. The drive spring may be attached at one end to the housing component and/or an additional housing component and at the other end to a component part coupled to the clutch element, e.g. the number sleeve. The torsion spring may be pre-wound upon assembly of a drug delivery device, such that it applies a torque to the clutch element when the mechanism is at zero units dialed.

Providing a resilient drive member, such as a torsion spring, generating the force or torque required for dose dispensing reduces the user applied forces for dose dispensing. This is especially helpful for users with impaired dexterity. In addition, the dial extension of the known manually driven devices, which is a result of the required dispensing stroke, may be omitted by providing the resilient member because merely a small triggering stroke may be necessary for releasing the resilient member.

The torsion spring may be formed from a helical wire with at least two different pitches. Preferably, both ends are formed from 'closed' coils, i.e. the pitch equals the wire diameter and each coil contacts the adjacent coil, while the central portion has 'open' coils, i.e. the coils do not contact each other.

Having both open and closed coils in the spring has the following advantages: When a dose is set, the torsion spring is usually charged. If all the coils were closed, winding up the spring would increase the length of the spring by one wire diameter for each turn, and so hook ends of the spring would no longer be aligned with their anchor points, which are e.g. on the number sleeve and the housing. The open coils allow the spring to compress to accommodate the additional turns of wire, without increasing the total length of the spring. Further, the open coils allow the spring to be compressed during assembly. For example, the spring is manufactured longer than the space available in the device. It is then compressed during assembly, ensuring that the axial positions of the hook ends are better aligned with their anchor points on the housing and the number sleeve. In addition, it is easier to manufacture the spring to a specified length if most of the coils are closed, as the length of these coils is only a function of the wire diameter. Following assembly, compression in the spring biases the number sleeve axially relative to the housing in a consistent direction, reducing the effects of geometric tolerances. The addition of closed coils at each end makes the springs less prone to tangling with each other when they are stored together between manufacture and assembly. Closed coils at the ends provide a flat surface for contact with the housing and number sleeve which is preferred.

In a preferred embodiment the drug delivery device comprises a gauge element, which is interposed between the housing and the number sleeve. The gauge element may have a second aperture, which is positioned with respect to the first aperture of the housing such that at least a part of the number sleeve is visible through the first and second apertures or windows. The gauge element may be axially guided within the housing and in threaded engagement with the number sleeve such that rotation of the number sleeve causes an axial displacement of the gauge element.

The position of the gauge element may thus be used to identify the actually set and/or dispensed dose. Different colours of sections of the gauge member may facilitate identifying the set and/or dispensed dose without reading numbers, symbols or the like on a display. As the gauge element is in threaded engagement with the number sleeve, rotation of the number sleeve causes an axial displacement of the gauge element relative to the number sleeve and relative to the housing. The gauge element may have the form of a shield or strip extending in the longitudinal direction of the device. As an alternative, the gauge element may be a sleeve. In an embodiment of the disclosure, the number sleeve is marked with a sequence of numbers or symbols and the gauge element comprises an aperture. With the number sleeve located radially inwards of the gauge element, this allows that at least one of the numbers or symbols on the number sleeve is visible through the aperture. In other words, the gauge element may be used to shield or cover a portion of the number sleeve and to allow view only on a limited portion of the number sleeve. This function may be in addition to the gauge element itself being suitable for identifying or indicating the actually set and/or dispensed dose.

In a preferred embodiment, the number sleeve, during dose setting, is adapted to undergo a mere rotational movement within the housing and relative to the housing. In other words, the number sleeve does not perform a translational movement during dose setting. This prevents that the number sleeve is wound out of the housing or that the housing has to be prolonged for covering the number sleeve within the housing.

In addition to the dose selector operable to set a dose the device may comprise a button operable to effect dose dispensing. If the button of the device is rotatable relative to the housing and rotationally locked to the number sleeve in its dose setting position and, in addition, is rotatable relative to the number sleeve and rotationally locked to the housing in its dose dispensing position, there is no relative rotational movement between the button and the dosage selector. Rotationally constraining the button to the housing during dose dispensing has the additional advantage that there is no friction due to relative rotation between a user's finger and the button. Further, this prevents unintended manipulation of the set dose during dispensing.

Further, the button may be used to generate a feedback signal. For example, a dispense clicker comprising a flexible arm and a toothed profile may be provided. According to a preferred embodiment, the flexible arm is provided on the clutch element and the toothed profile is provided on the button. In other words, the dispense clicker is provided by the button and the clutch element.

Preferably, the toothed profile is a ring of radially inwards directed ratchet teeth. The clicker arm may have various configurations, for example a bent configuration with free end having a tip extending in the radially outwards direction for interaction with the toothed profile. Preferably, the clicker arm is a compliant cantilever clicker arm. An embodiment of the present disclosure includes a drug delivery device in which tactile feedback is provided during dose dispense via the compliant cantilever clicker arm integrated into the clutch plate. This arm interfaces radially with ratchet features on the inner surface of the button, whereby the ratchet tooth spacing corresponds to the number sleeve rotation required for a single increment dispense. Preferably, as the number sleeve rotates and the button is rotationally coupled to the housing during dispensing, the ratchet features engage with the clicker arm to produce an audible click with each dose increment delivered.

In an embodiment of the disclosure, the clutch element comprises the ratchet clutch features for engaging the drive sleeve and may have the form of a plate or disk. As an alternative, the clutch element may have the form of a sleeve. The clutch element is axially interposed between the sleeve and the button such that axial movement of the button in a first direction, preferably in the distal direction, is transferred to the sleeve via the clutch element and axial movement in the opposite, preferably proximal, direction is transferred to the button via the clutch element. As an alternative, the clutch element may be a unitary part of the button. In a preferred embodiment the clutch element is permanently or releasably coupled to further component parts of a drug delivery device, for example a number sleeve and/or a dose setting member. The clutch element may be a multi-functional element having in addition to the interface with the drive sleeve and the interface with the button e.g. a clicker feature and/or at least one further interface.

The button is preferably a user operable element located proximally from the sleeve and the clutch element. When used in a drug delivery device, the button may extend from the proximal end of the device and, preferably, does not change its axial position during dose setting. The button is preferably coupled to a user operable dose setting member and may be releasably coupled to a number sleeve component and/or a stationary housing component. In an alternative embodiment, the button may be part of a dose setting arrangement or may be the dose setting member. The button is preferably a multi-functional element having in addition to the above features the clicker feature.

The stationary housing component is a fixed basis for relative movements of the axially movable drive sleeve, the clutch element and the button. The housing may be part of a multi-component housing or may be the only housing component of a drug delivery device. In a preferred embodiment, the stationary housing comprises an axial support or bearing for the clutch spring and means for releasably engaging the sleeve. Preferably, the housing comprises one or more teeth, for example a ring of teeth, engaging one or more corresponding teeth, preferably also a ring of teeth, of the drive sleeve depending on the relative axial position of the drive sleeve with respect to the housing. In other words, the engagement means or teeth mesh and interlock in a first, e.g. proximal, position of the drive sleeve relative to the housing and are disengaged, thus allowing relative rotation, in a second, e.g. distal, position of the drive sleeve relative to the housing. The housing may be a multi-functional element having in addition to the above features e.g. a clicker feature and/or an interface to a piston rod.

In a drug delivery device at least one dose setting member may be provided that can be operated to set a dose, wherein actuation of the button causes dispensing of the set dose. Preferably, the operation of the at least one dose setting member strains the drive spring and actuation of the button allows the drive spring to relax and thereby rotate the clutch element, the drive sleeve and the piston rod relative to the housing which causes the piston rod to advance in the distal direction relative to the housing.

It is preferred if the device is suitable for dispensing variable, user-selectable, doses of medicament. The device may be a disposable device, i.e. a device which does not provide for an exchange of an empty cartridge.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. Preferably, the limits for the minimum dose and the maximum dose are provided by hard stop features. The limiter mechanism may comprise a first rotational stop on the number sleeve and a first counter stop on the gauge element, which abut in the minimum dose (zero) position, and a second rotational stop on the number sleeve and a second counter stop on the gauge element, which abut in the maximum dose position. As the number sleeve rotates relative to the gauge element during dose setting and during dose dispensing, these two components are suitable to form a reliable and robust limiter mechanism.

The drug delivery device may further comprise a last dose protection mechanism for preventing the setting of a dose, which exceeds the amount of liquid left in a cartridge. This has the advantage that the user knows how much will be delivered before starting the dose delivery. It also ensures that dose delivery stops in a controlled manner without the bung entering the neck portion of the cartridge where the diameter is smaller which may result in an underdose. In a preferred embodiment, this last dose protection mechanism only detects the medicament remaining in the cartridge when the cartridge contains less than the maximum dose (e.g. 120 IU). For example, the last dose protection mechanism comprises a nut member interposed between the drive member and a component which rotates during dose setting and dose dispensing. The component which rotates during dose setting and dose dispensing may be the number sleeve or a dial sleeve rotationally constrained to the number sleeve. In a preferred embodiment, the number sleeve rotates during dose setting and during dose dispensing, whereas the drive member only rotates during dose dispensing together with the number sleeve. Thus, in this embodiment, the nut member will only move axially during dose setting and will remain stationary with respect to these components during dose dispensing. Preferably, the nut member is threaded to the drive member and splined to the number sleeve and/or a dial sleeve. As an alternative, the nut member may be threaded to the number sleeve and/or a dial sleeve and may be splined to the drive member. The nut member may be a full nut or a part thereof, e.g. a half nut.

Preferably, the piston rod (lead screw) advances by a fixed displacement for each revolution of the axially movable drive sleeve. In other embodiments, the rate of displacement may vary. For example, the piston rod may advance a large displacement per revolution to dispense a first amount of medicament from the cartridge and then a smaller displacement per revolution to dispense the rest of the cartridge. This is advantageous, as it can compensate for the fact that the first dose dispensed from the cartridge often has a lower volume than other doses, for a given displacement of the mechanism. If the pitch is equal on the threads of the housing and the piston rod, the piston rod advances a fixed amount for every revolution of the movable sleeve. However, if in an alternative embodiment the first turn of the thread on the piston rod has a large pitch and the other turns have a small pitch, during the first revolution the piston rod displacement depends on the large pitch of the first turn of thread on the piston rod, so it displaces a large amount per revolution. For subsequent revolutions the piston rod displacement depends on the smaller pitch of the piston rod thread, so it displaces a smaller amount. If, in a further embodiment, the housing thread has a larger pitch than the piston rod, during the first revolution, the piston rod displacement depends on the pitch of the housing thread, so it displaces a large amount per revolution. For subsequent revolutions the piston rod displacement depends on the pitch of the piston rod thread, so it displaces a smaller amount.

The aperture in the housing and/or the aperture in the gauge element may be a simple opening. However, it is preferred if at least one aperture is closed by a window or lens which prevents intrusion of dirt and/or may increase legibility of e.g. numbers on the number sleeve, for example due to a magnification.

According to a preferred embodiment of the disclosure the number sleeve is clipped to the housing at the distal end. This reduces the geometric tolerances for the gauge position. In other words, the number sleeve is preferably axially fixed relative to the housing but allowed to rotate relative thereto.

Preferably, the drive sleeve is clipped inside the number sleeve to retain it during subsequent assembly steps. In an alternative embodiment, the drive sleeve is clipped to the housing instead to retain it during subsequent assembly steps. In both embodiments, the drive sleeve is free to move beyond its assembled position when the button is pressed. The clips prevent movement in the disassembly direction, but do not prevent further movement, e.g. for dispense.

The lens and the window in the gauge may be incorporated into the housing using a 'twin-shot' moulding technology. For example, they are moulded during a 'first shot' in a translucent material, and the outer cover of the housing is moulded during a 'second shot' in an opaque material.

If there is only one threaded portion on the gauge element this reduces the length of this component.

Preferably, the tooth geometry on the clutch plate and the drive sleeve is chosen such that the dialing torque is low. Further, the clutch plate may comprise a dispense clicker which interferes with clicker teeth on the button.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-N H2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically Acceptable Solvates are for Example Hydrates.

Non-limiting, exemplary embodiments of the disclosure will now be described with reference to the accompanying drawings, in which:

FIG. 4a shows an enlarged sectional view of a detail of the device of FIG. 1 in the dose setting mode;

FIG. 4b shows an enlarged sectional view of a detail of the device of FIG. 1 in the dose dispensing mode;

FIG. 5 shows an interface between the number sleeve and the button of the device of FIG. 1;

Figure 1:
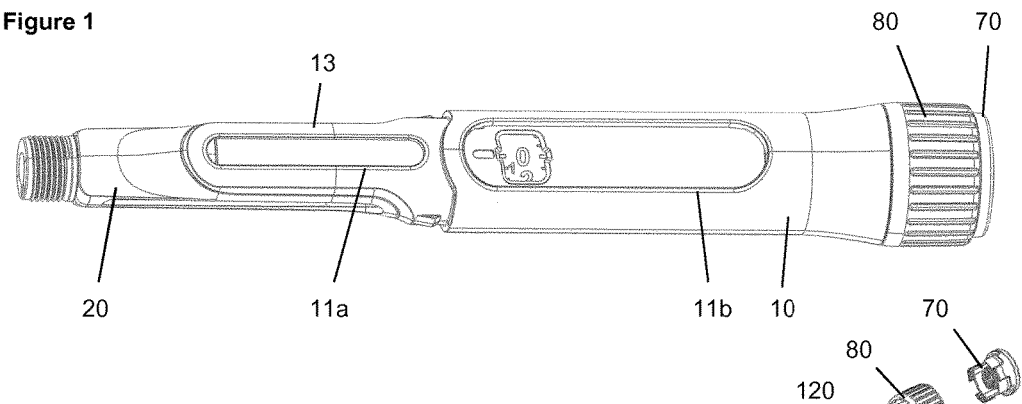
FIG. 1 shows a top view of the drug delivery device of the present disclosure invention in the minimum dose position.
Figure 7A:
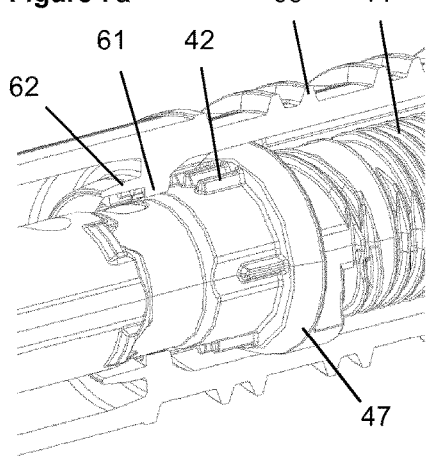
Figure 8:
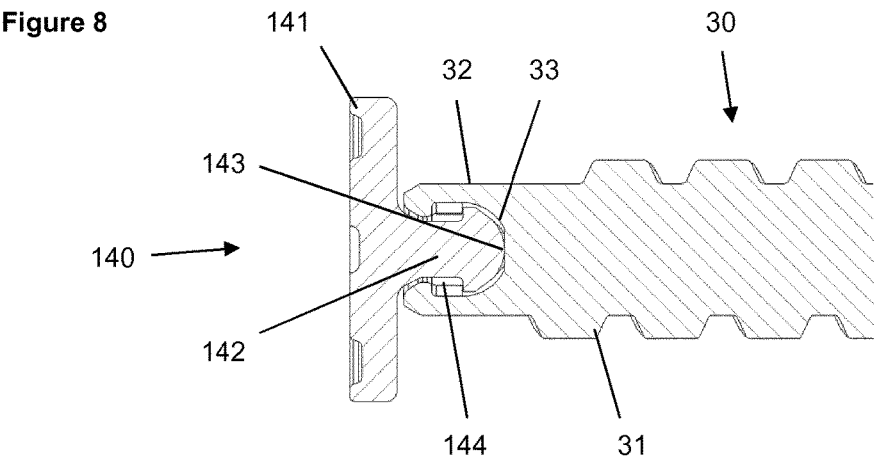
Figure 12A:
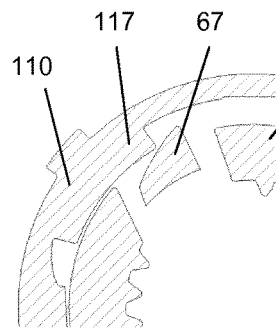
Figure 12B:
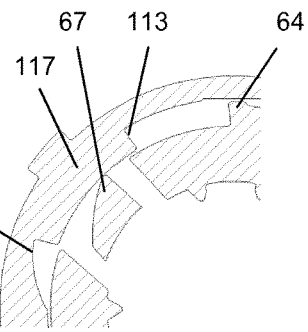
Figure 12C:
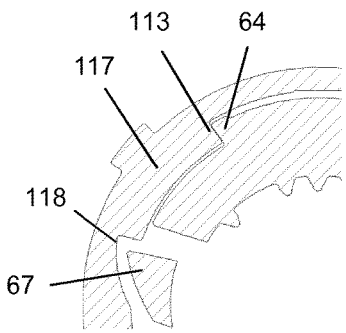
Figure 13:
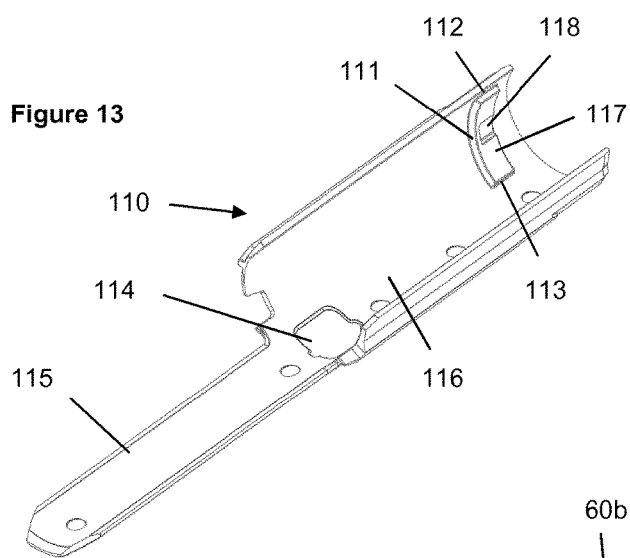
Figure 14:
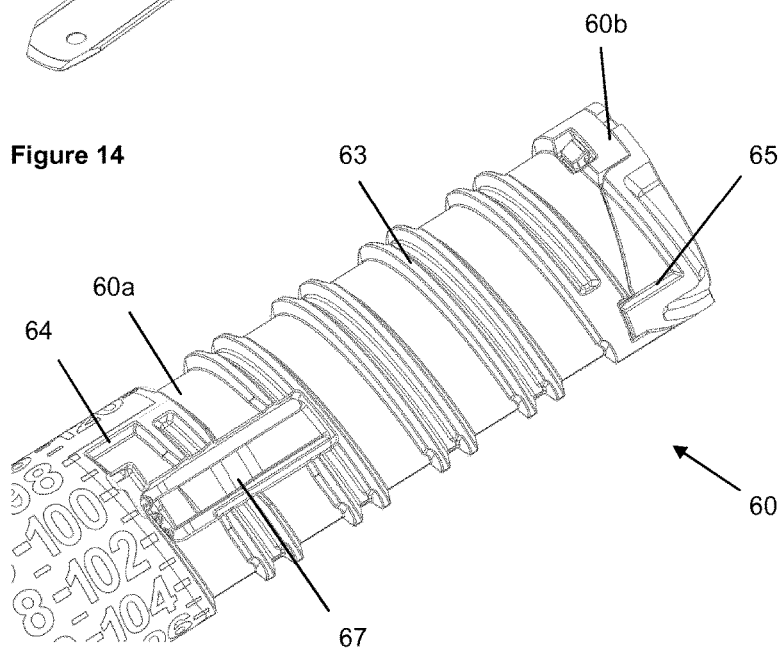
Figure 15:
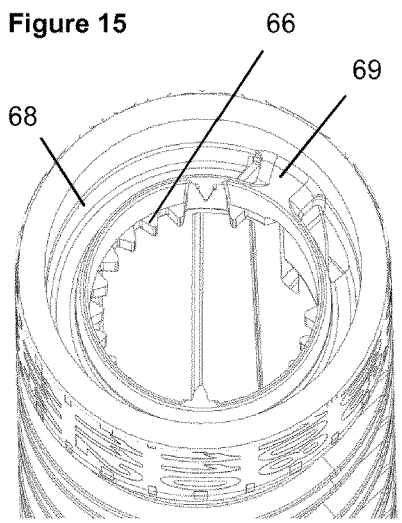
Figure 16:
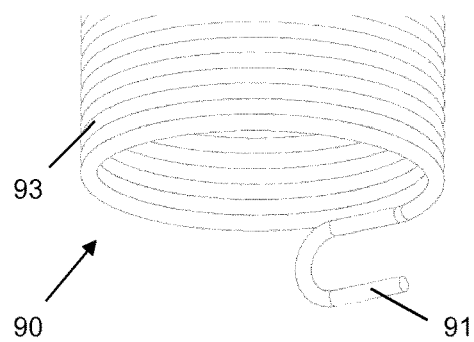
Figure 17A:
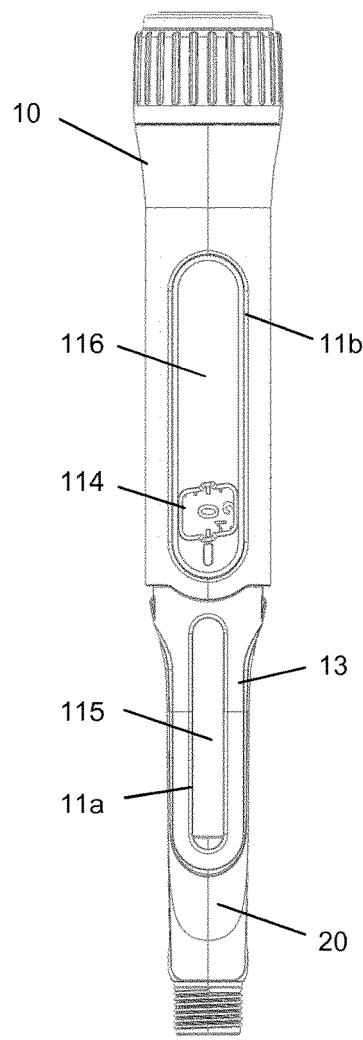
Figure 18:
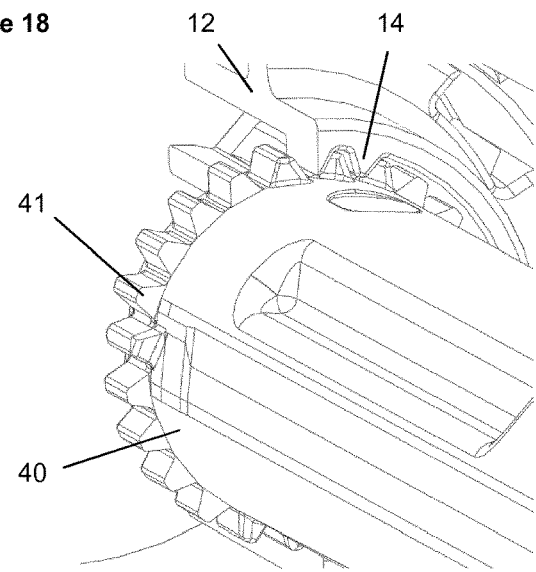
Figure 19:
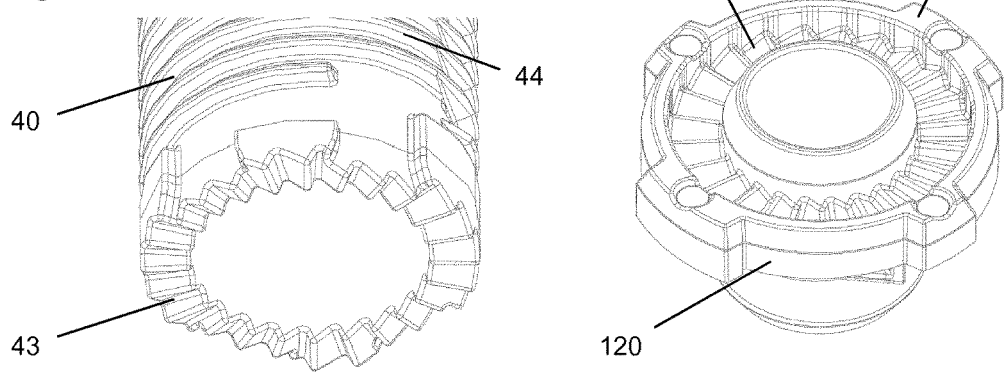
Figure 20:
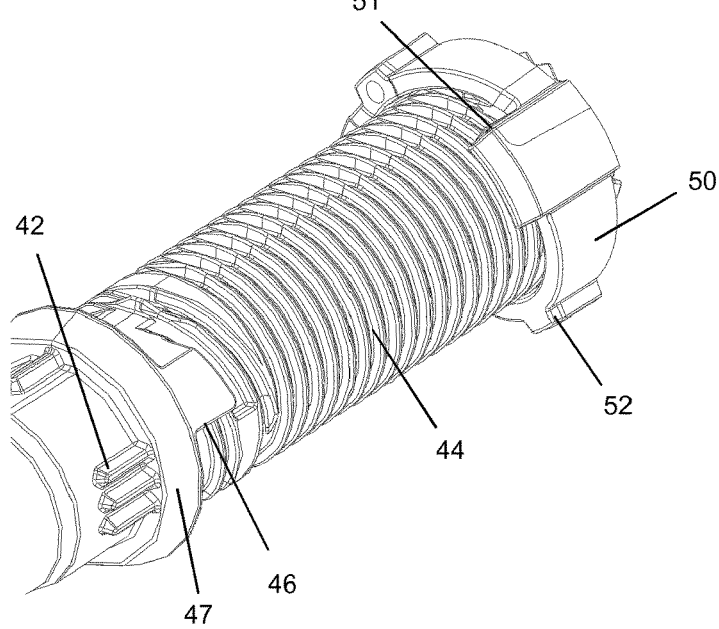

FIG. 7a, b show an interface between the number sleeve and the drive sleeve of the device of FIG. 1 in the dose setting mode and in the dose dispensing mode;

FIG. 8 shows an interface between the piston rod and a bearing of the device of FIG. 1;

FIG. 9 shows an interface between the clutch plate and the button of the device of FIG. 1;

FIG. 10 shows in a sectional view the components of an end of dose clicker of the device of FIG. 1;

FIGS. 11a-c show in enlarged views the sequence of generating a click at the end of dose dispensing of the device of FIG. 1;

FIGS. 12a-c show in enlarged sectional views the sequence of generating a click at the end of dose dispensing of the device of FIG. 1;

FIG. 13 shows the gauge element of the device of FIG. 1;

FIG. 14 shows a portion of the number sleeve of the device of FIG. 1;

FIG. 15 shows a further portion of the number sleeve of the device of FIG. 1;

FIG. 16 shows a portion of the drive spring of the device of FIG. 1;

FIG. 17a, b show top views of the device of FIG. 1 with 0 units dialed and with 96 units dialed;

FIG. 18 shows an interface between the housing and the drive sleeve of the device of FIG. 1;

FIG. 19 shows an interface between the clutch plate and the drive sleeve of the device of FIG. 1;

FIG. 20 shows a last dose mechanism of the device of FIG. 1;

FIG. 21 shows the torsion spring of the device of FIG. 1; and

FIGS. 22a-c show different embodiments of the threads between the piston rod and the housing of the device of FIG. 1.

Figure 2:
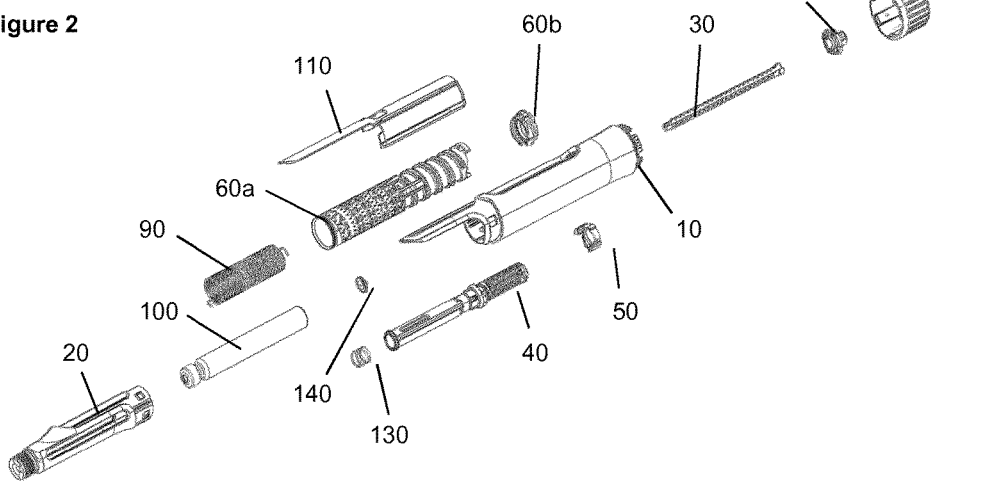
FIG. 2 shows an exploded view of the components of the device of FIG. 1.
Figure 3:
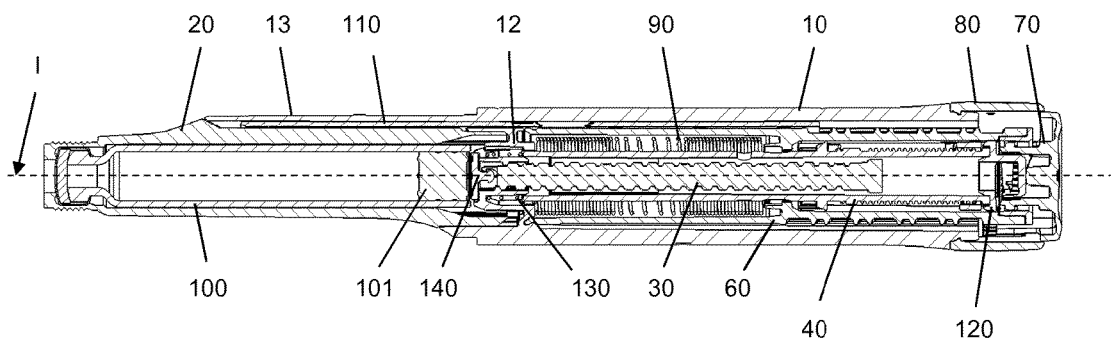
FIG. 3 shows a sectional view of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis I of the mechanism which is shown in FIG. 3.

The housing 10 or body is a generally tubular element having a proximal end with an enlarged diameter. The housing 10 provides location for the liquid medication cartridge 100 and cartridge holder 20, windows 11a, 11b for viewing the dose number on the number sleeve 60 and the gauge element 110, and a feature on its external surface, e.g. a circumferential groove, to axially retain the dose selector 80. A flange-like or cylindrical inner wall 12 comprises an inner thread engaging the piston rod 30. The housing 10 further has at least one internal, axially orientated slot or the like for axially guiding the gauge element 110. In the embodiment shown in the Figures, the distal end is provided with an axially extending strip 13 partly overlapping cartridge holder 20. The Figures depict the housing 10 as a single housing component. However, the housing 10 could comprise two or more housing components which may be permanently attached to each other during assembly of the device.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the inner wall 12 of housing 10. The lead screw 30 is an elongate member with an outer thread 31 (FIG. 3) engaging the corresponding thread of the inner wall 12 of housing 10. The thread 31 may have a large lead-in, for example a wedge shape form, at its distal end to engage a corresponding housing thread form on the first rotation. The interface comprises at least one longitudinal groove or track and a corresponding protrusion or spline 45 of the driver 40. At its distal end, the lead screw 30 is provided with an interface for clip attachment of the bearing 140. In the present embodiment, this interface comprises two clip arms 32 extending in the distal direction defining an insertion space between them for insertion of a bearing 140 interface. As an alternative, the interface may comprise only one single clip arm extending more than 180° about the longitudinal axis, or may comprise one or several clip arms 32. The clip arm(s) 32 may have a bent form with a recessed clip portion as shown in FIG. 8. Preferably, the clip arm(s) form a cylindrical outer face having a diameter equal to or smaller than the outer diameter of the lead screw 30 at the base of the groove (flute base) of the outer thread 31. A concave contact surface 33 is provided between the clip arms 32 for abutment of a corresponding portion of bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

A splined tooth interface with the housing 10 prevents rotation of the drive sleeve 40 during dose setting. This interface which is shown in FIG. 18 in detail comprises a ring of radially extending outer teeth 41 at the distal end of drive sleeve 40 and corresponding radially extending inner teeth 14 of the housing component 10. When the button 70 is pressed, these drive sleeve 40 to housing 10 spline teeth 14, 41 are disengaged allowing the drive sleeve 40 to rotate relative to housing 10.

Figure 7B:
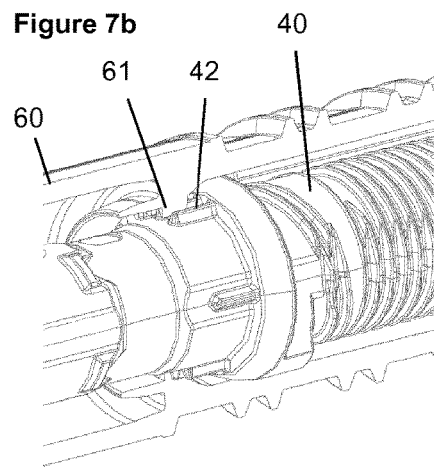

A further splined tooth interface with the number sleeve 60 is not engaged during dialing, but engages when the button 70 is pressed, preventing relative rotation between the drive sleeve 40 and number sleeve 60 during dispense. In the preferred embodiment shown in FIGS. 7a and 7b this interface comprises inwardly directed splines 61 on a flange 62 on the inner surface of the number sleeve 60 and a ring of radially extending outer splines 42 of drive sleeve 40. The corresponding splines 61, 42 are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

Preferably, the splines 61, 42 are arranged such that they are decoupled when teeth 41 of drive sleeve 40 and inner teeth 14 of housing component 10 mesh and engage when teeth 41 and inner teeth 14 disengage. In a preferred embodiment the splines 61, 42 are longer in the axial direction compared with teeth 41, 14. This allows engagement of the splines 61, 42 shortly before disengagement of teeth 41, 14. In other words, the splines 61, 42 and the teeth 41, 14 are designed and arranged such that actuation of the button 70 rotationally constrains the drive sleeve 40 to the number sleeve 60 before the drive sleeve 40 is allowed to rotate relative to housing 10. Similarly, as the button 70 is released after dose dispensing axial movement of the drive sleeve 40 first rotationally constrains the drive sleeve 40 to the housing and thereafter decouples splines 61, 42. As an alternative to the corresponding splines 61, 42 teeth may be provided. As a further alternative or in addition to splines 61, 42, drive sleeve 40 and number sleeve 60 may be rotationally coupled to each other during dose dispensing via clutch plate 120.

An interface of the drive sleeve 40 which is shown in FIG. 19 comprises a ring of ratchet teeth 43 located at the proximal end face of drive sleeve 40 and a ring of corresponding ratchet teeth 121 of clutch plate 120.

The driver 40 has a threaded section 44 providing a helical track for the nut 50 (FIG. 20). In addition, a last dose abutment or stop 46 is provided which may be the end of the thread 44 track or preferably a rotational hard stop for interaction with a corresponding last dose stop 51 of nut 50, thus limiting movement of the nut 50 on the thread 44. At least one longitudinal spline 45 engages a corresponding track of the lead screw 30. Further, the drive sleeve is provided with a ramp 47 interacting with a clicker arm 67 when the drive sleeve 40 is in its distal position during dose dispensing, i.e. when button 70 is depressed.

The last dose nut 50 is located between the number sleeve 60 and the drive sleeve 40. It is rotationally constrained to the number sleeve 60, via a splined interface (splines 52 on nut 50). It moves along a helical path relative to the drive sleeve 40, via a threaded interface (thread 44), when relative rotation occurs between the number sleeve 60 and drive sleeve 40 which is during dialing only. This is shown in FIG. 20. As an alternative, the nut 50 may be splined to the driver 40 and threaded to the number sleeve 60. In the embodiment shown in the Figures, the nut 50 is a full nut, but in alternative embodiments it may be a half nut, i.e. a component extending approximately 180° around the center axis of the device. A last dose stop 51 is provided engaging stop 46 of drive sleeve 40 when a dose is set corresponding to the remaining dispensable amount of medicament in the cartridge 100.

The dose indicator or number sleeve 60 is a tubular element as shown in FIGS. 2 and 3. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may be seen as a dose setting member.

For manufacturing reasons the number sleeve 60 of the embodiment shown in the Figures comprises a number sleeve lower 60a which is rigidly fixed to a number sleeve upper 60b during assembly to form the number sleeve 60. Number sleeve lower 60a and number sleeve upper 60b are separate components only to simplify number sleeve 60 mould tooling and assembly. As an alternative, the number sleeve 60 may be a unitary component. The number sleeve 60 is constrained to the housing 10 by features towards the distal end to allow rotation but not translation. The number sleeve lower 60a is marked with a sequence of numbers, which are visible through the gauge element 110 and the openings 11a, 11b in the housing 10, to denote the dialed dose of medicament.

Further, the number sleeve lower 60a has a portion with an outer thread 63 engaging the gauge element 110. End stops 64, 65 are provided at the opposite ends of thread 63 to limit relative movement with respect to the gauge element 110.

Clutch features which have the form of a ring of splines 66 in the embodiment of FIG. 5 are provided inwardly directed on number sleeve upper 60b for engagement with splines 73 of the button 70 during dose setting and dose correction. A clicker arm 67 is provided on the outer surface of number sleeve 60 which interacts with the drive sleeve 40 and the gauge member 110 for generating a feedback signal. In addition, the number sleeve lower 60a is rotationally constrained to the nut 50 and to the clutch plate 120 via a splined interface comprising at least one longitudinal spline.

An interface for attachment of the torsion spring 90 to the number sleeve lower 60a comprises large lead-ins and a groove feature 68 with a pocket 69 or anchor point for receiving a first coil or hook portion of the spring. The groove 68 has an end feature in the form of a ramp that is in interference with the hook portion 91 of the spring. The design of the groove 68 is such that the spring 90 may be received within the pocket 69 without interfering with the gauge element 110.

Figure 6:
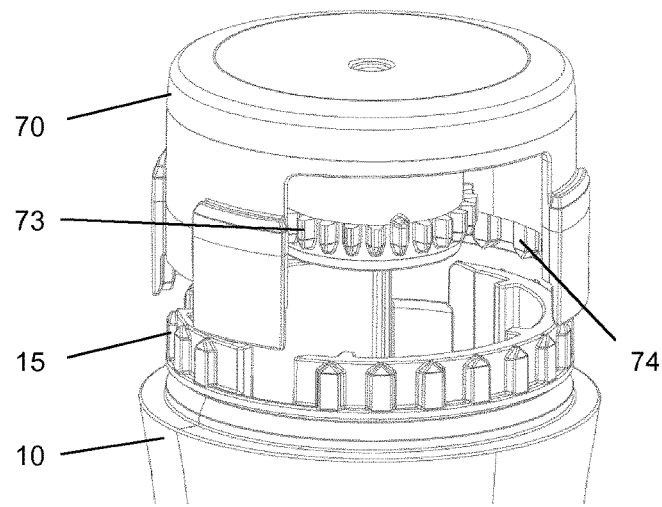
FIG. 6 shows an interface between the housing and the button of the device of FIG. 1.

The button 70 which forms the proximal end of the device is permanently splined to the dose selector 80. A central stem 71 extends distally from the proximal actuation face of the button 70. The stem 71 is provided with a flange 72 carrying the splines 73 for engagement with splines 66 of the number sleeve upper 60b (FIG. 5). Thus, it is also splined via splines 66, 73 (FIG. 5) to the number sleeve upper 60b when the button 70 is not pressed, but this spline interface is disconnected when the button 70 is pressed. The button 70 has a discontinuous annular skirt with splines 74. When the button 70 is pressed, splines 74 on the button 70 engage with splines on the housing 10 (FIG. 6), preventing rotation of the button 70 (and hence the dose selector 80) during dispense. These splines 74, 15 disengage when the button 70 is released, allowing a dose to be dialed. Further, a ring of ratchet teeth 75 is provided on the inner side of flange 72 (FIG. 9) for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end to the housing 10 and at the other end to the number sleeve 60. The torsion spring 90 is located inside the number sleeve 60 and surrounds a distal portion of the drive sleeve 40. As shown in FIG. 16, the spring has a hook 91 at one end for attachment on the number sleeve 60. A similar hook end 92 is provided at the opposite end for attachment on the housing 10. The torsion spring 90 is pre-wound upon assembly, such that it applies a torque to the number sleeve 60 when the mechanism is at zero units dialed. The action of rotating the dose selector 80, to set a dose, rotates the number sleeve 60 relative to the housing 10, and charges the torsion spring 90 further.

The torsion spring 90 is formed from a helical wire with at least two different pitches. In FIG. 21, both ends are formed from 'closed' coils 93, i.e. the pitch equals the wire diameter and each coil contacts the adjacent coil. The central portion has 'open' coils 94, i.e. the coils do not contact each other.

The cartridge 100 is received in cartridge holder 20 (FIG. 3). The cartridge 100 may be a glass ampoule having a moveable rubber bung 101 at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing back-winding of the lead screw 30 and the resetting of nut 50.

The gauge element 110 is constrained to prevent rotation but allow translation relative to the housing 10 via a splined interface. The gauge element 110 has a helical feature 111 on its inner surface which engages with the helical thread cut in the number sleeve 60 such that rotation of the number sleeve 60 causes axial translation of the gauge element 110. This helical feature on the gauge element 110 also creates stop abutments 112, 113 against the end of the helical cut in the number sleeve 60 to limit the minimum and maximum dose that can be set.

The gauge element 110 has a generally plate or band like component having a central aperture 114 or window and two flanges 115, 116 extending on either side of the aperture. The flanges 115, 116 are preferably not transparent and thus shield or cover the number sleeve 60, whereas the aperture 114 or window allows viewing a portion of the number sleeve lower 60a. Further, gauge element 110 has a cam 117 and a recess 118 (FIG. 11a-12c) interacting with the clicker arm 67 of the number sleeve 60 at the end of dose dispensing.

As can be seen in FIGS. 9 and 19, the clutch plate 120 is a ring-like component. The clutch plate 120 is splined to the number sleeve 60 via splines 122. It is also coupled to the drive sleeve 40 via a ratchet interface (ratchet teeth 43, 121). The ratchet provides a detented position between the number sleeve 60 and drive sleeve 40 corresponding to each dose unit, and engages different ramped tooth angles during clockwise and anti-clockwise relative rotation. A clicker arm 123 is provided on the clutch plate 120 for interaction with ratchet features 75 of the button.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface (ratchet teeth 43, 121) is always engaged. In the 'at rest' position, it also ensures that the button splines 73 are engaged with the number sleeve splines 66, and the drive sleeve teeth 41 are engaged with teeth 14 of the housing 10.

The bearing 140 is axially constrained to the piston rod 30 and acts on the bung 101 within the liquid medicament cartridge. It is axially clipped to the lead screw 30, but free to rotate. The bearing 140 comprises a disc 141 having a stem 142 extending in the proximal direction. The stem 142 has at its proximal end a convex contact surface 143. In addition, a recessed portion 144 is provided on the stem 142. The curvature of the convex contact surface 143 and the concave contact surface 33 is chosen such that the contact diameter between the bearing 140 and lead screw 30 is small to minimize the frictional losses at this interface. The design of the clip interface between bearing 140 and lead screw 30 permits the lead screw 30 to be assembled axially, from the proximal end and through the thread engagement to the housing 10, which simplifies assembly. In addition, this design allows a simple "open and shut" mould tooling for both components.

With the device in the 'at rest' condition as shown in FIGS. 4a and 17a, the number sleeve 60 is positioned against its zero dose abutment 64, 113 with the gauge element 110 and the button 70 is not depressed. Dose marking '0' on the number sleeve 60 is visible through the windows 11b and 114 of the housing 10 and gauge element 110, respectively.

The torsion spring 90, which has a number of pre-wound turns applied to it during assembly of the device, applies a torque to the number sleeve 60 and is prevented from rotating by the zero dose abutment 64, 113. It is also possible to 'back-wind' the mechanism slightly due to an offset between the zero dose stop 64, 113 and the angular offset of the drive sleeve 40 spline teeth. This has the effect of preventing possible weepage when a dose is dialed and the zero dose abutment is disengaged.

The automated assembly of the torsion spring 90 into the number sleeve 60 can be achieved by incorporating large lead-ins and a groove feature to the number sleeve 60. As the torsion spring 90 is rotated during assembly, the hook end form 91 locates in the groove feature before engaging the anchor point in the number sleeve 60. To help to prevent the torsion spring 90 disengaging the anchor point 69 during subsequent assembly steps it is possible to create an interference between the torsion spring 90 and the number sleeve 60, or a one-way clip feature.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialed dose. The gauge element 110 has flanges 115, 116 either side of the window area 114 which cover the numbers printed on the number sleeve 60 adjacent to the dialed dose to ensure only the set dose number is made visible to the user.

A specific feature of this disclosure is the inclusion of a visual feedback feature in addition to the discrete dose number display typical on devices of this type. The distal end (flange 115) of the gauge element 110 creates a sliding scale through a small window 11a in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured component underneath. Alternatively, the revealable element may be printed with coarse dose numbers or other indices to provide more precise resolution. In addition, the gauge display simulates a syringe action during dose set and dispense.

Figure 17B:
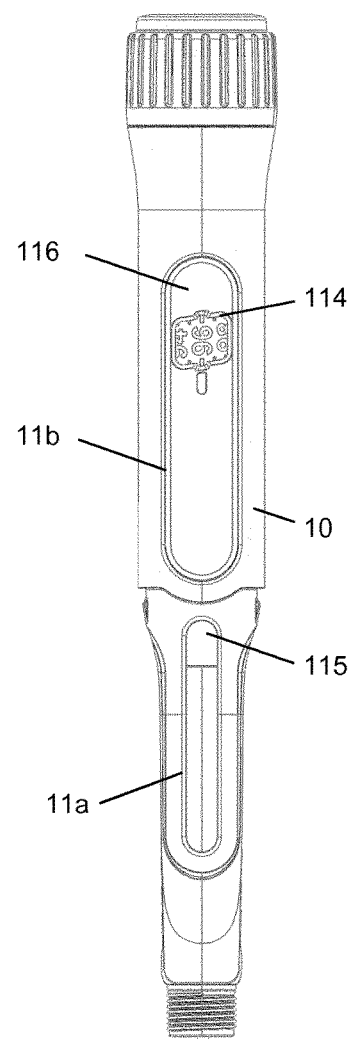

The openings 11a, 11b in the housing 10 allow the user to view the gauge feature and number display as shown in FIGS. 17a and 17b. To reduce dust ingress and prevent the user from touching moving parts, these openings 11a, 11b are covered by translucent windows. These windows may be separate components, but in this embodiment they are incorporated into the housing 10 using 'twin-shot' moulding technology. A first shot of translucent material forms the internal features and the windows 11a, 11b, and then a 'second shot' of opaque material forms the outer cover of the housing 10.

The mechanism utilises a dose selector 80 with an increased diameter relative to the housing 10 which aids dialing although this is not a requirement of the mechanism. This feature is particularly useful (but not essential) for an auto-injector mechanism where a power supply is charged during dose setting and the torque required to turn the dose selector 80 may be higher than for a non-auto injector device.

The drive sleeve 40 is prevented from rotating as the dose is set and the number sleeve 60 rotated, due to the engagement of its splined teeth 41 with teeth 14 of the housing 10. Relative rotation must therefore occur between the clutch plate 120 and drive sleeve 40 via the ratchet interface 43, 121.

The user torque required to rotate the dose selector 80 is a sum of the torque required to wind up the torsion spring 90, and the torque required to overhaul the ratchet interface 43, 121. The clutch spring 130 is designed to provide an axial force to the ratchet interface 43, 121 and to bias the clutch plate 120 onto the drive sleeve 40. This axial load acts to maintain the ratchet teeth engagement of the clutch plate 120 and drive sleeve 40. The torque required to overhaul the ratchet 43, 121 in the dose set direction is a function of the axial load applied by the clutch spring 130, the clockwise ramp angle of the ratchet teeth 43, 121, the friction coefficient between the mating surfaces and the mean radius of the ratchet interface 43, 121.

As the user rotates the dose selector 80 sufficiently to increment the mechanism by one increment, the number sleeve 60 rotates relative to the drive sleeve 40 by one ratchet tooth. At this point the ratchet teeth 43, 121 re-engage into the next detented position. An audible click is generated by the ratchet re-engagement, and tactile feedback is given by the change in torque input required.

Relative rotation of the number sleeve 60 and the drive sleeve 40 is allowed as splines 42, 61 are disengaged during dose setting. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface 43, 121 between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface 43, 121 between the number sleeve 60 and drive sleeve 40 is repeated for each dose increment. Additional energy is stored within the torsion spring 90 for each dose increment and audible and tactile feedback is provided for each increment dialed by the re-engagement of the ratchet teeth. The torque required to rotate the dose selector 80 increases as the torque required to wind up the torsion spring 90 increases.

The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment 65 on the maximum dose abutment 112 of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment 51 with stop face 46 of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface 43, 121 between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines 74 on the button 70 engage with splines 15 on the housing 10, preventing rotation of the button 70 (and hence the dose selector 80) during dispense. As the button 70 is stationary during dispense, it can be used in the dispense clicker mechanism as shown in FIG. 9. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface 42, 61 between the drive sleeve 40 and number sleeve 60 as shown in FIG. 7a (splines 42, 61 disengaged) and 7b (splines 42, 61 engaged), preventing relative rotation between the drive sleeve 40 and number sleeve 60 during dispense. The splined tooth interface 41, 14 between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment 64, 113 stops the mechanism.

The bearing 140 is axially clipped to the piston rod 30, but free to rotate. Since the bearing 140 is in direct contact with the bung 101, it does not rotate as the piston rod 30 rotates and advances during dose dispense. As described above, the contact diameter between the bearing 140 and piston rod 30 is small to minimise the frictional losses at this interface. The design of the piston rod 30 and bearing 140 eliminates delicate clip features or large contact diameters present on previous concepts. This embodiment also allows the piston rod 30 to be assembled axially, from the proximal end and through the thread engagement to the housing 10, which simplifies assembly.

Tactile feedback during dose dispense is provided via the compliant cantilever clicker arm 123 integrated into the clutch plate 120. This arm 123 interfaces radially with ratchet features 75 on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features 75 engage with the clicker arm 123 to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines 14, 41 between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialing only.

Once the delivery of a dose is stopped, by the number sleeve 60 returning to the zero dose abutment, the user may release the button 70, which will re-engage the spline teeth 14, 41 between the drive sleeve 40 and housing 10. The mechanism is now returned to the 'at rest' condition.

It is possible to angle the spline teeth 14, 41 on either the drive sleeve 40 or housing 10 so that when the button 70 is released the re-engagement of the spline teeth 14, 41 fractionally 'backwinds' the drive sleeve 40 thereby removing the engagement of the number sleeve 60 to the zero dose stop abutment on the gauge element 110. This compensates for the effect of clearances in the mechanism (for example due to tolerances) which could otherwise lead to slight advancement of the piston rod 30 and medicament dispense when the device is dialed for the subsequent dose due to the number sleeve 60 zero dose stop not restraining the mechanism and instead the restraint returning to the splines between the drive sleeve 40 and housing 10.

At the end of dose dispensing, additional audible feedback is provided in the form of a 'click', distinct from the 'clicks' provided during dispense, to inform the user that the device has returned to its zero position via the interaction of the clicker arm 67 on the number sleeve 60 with the ramp 47 on the drive sleeve 40 and the cam 117 and the recess 118 on the gauge element 110. This embodiment allows feedback to only be created at the end of dose delivery and not created if the device is dialed back to, or away from, the zero position.

FIG. 11a shows the position of the click features when the device is in the 'at rest' condition, with zero units dialed and the button 70 not depressed. It can be seen that the cam feature 117 on the gauge element 110 does not contact the clicker arm 67 on the number sleeve 60 when the button 70 is in the 'at rest' condition, so during storage or dialing the clicker arm 67 is not deflected.

During dialing, the gauge element 110 translates in the proximal direction, so the cam 117 is no longer aligned axially with the clicker arm 67. At the start of dose delivery when the drive sleeve 40 translates in the distal direction, the ramp 47 on the drive sleeve 40 pushes the clicker arm 67 radially outwards. During dose delivery, the gauge element 110 translates back in the distal direction, and towards the end of dose delivery, the clicker arm 67 contacts the cam 117 on the gauge element 110. For small doses, the cam 117 and clicker arm 67 will be in contact at the start of the dose. FIG. 11b to 12c show the component interactions. After dose delivery, the button 70 is released and the end of dose mechanism returns to its 'at rest' position.

In FIG. 11b a dose is dialed and approximately one full dial turn is applied to number sleeve 60. Gauge element 110 is axially translated away from zero unit position, so that cam 117 is no longer aligned axially with clicker arm 67. FIG. 11c shows the start of dispensing, when button 70 is depressed to initiate dose dispense and which causes the drive sleeve 70 to translate axially. Ramp 47 on the drive sleeve 40 pushes clicker arm 67 radially out and into radial alignment with cam 117 on the gauge element 110.

FIG. 12a shows the mechanism at the end of dose dispensing with approximately 4 units remaining. The gauge element 110 returns axially towards its zero unit position, so that cam 117 aligns axially with clicker arm 67. Rotation of number sleeve 60 causes clicker arm 67 to contact cam 117 such that clicker arm 67 is pushed radially inwards. With approximately 2 units remaining the number sleeve 60 rotates further and clicker arm 67 follows the profile of cam 117 (FIG. 12b). This radial deflection 'charges' clicker arm 67 storing elastic energy. In FIG. 12c dispensing is completed as the number sleeve 60 reaches its zero unit rotational position. The clicker arm 67 drops off the sharp edge of cam 117 into recess 118. Elastic energy is released causing clicker arm 67 to spring radially outwards to contact cam 117 and create a distinct 'click'.

In the principal embodiment of this disclosure, the lead screw 30 advances by a fixed displacement for each revolution of the drive sleeve 40. In other embodiments, the rate of displacement may vary. For example, the lead screw 30 may advance a large displacement per revolution to dispense a first amount of medicament from the cartridge 100 and then a smaller displacement per revolution to dispense the rest of the cartridge 100. This is advantageous, as it can compensate for the fact that the first dose dispensed from the cartridge 100 often has a lower volume than other doses, for a given displacement of the mechanism.

FIG. 22 shows three embodiments with the threads 16 of the housing 10 and the threads 31 of the lead screw 30 projected around the circumference. Arrow R indicates the direction of revolution of the lead screw 30 with respect to housing 10 for all three views.

View (a) shows the principal embodiment, where the pitch is equal on the housing 10 and lead screw 30, so the lead screw 30 advances a fixed amount for every revolution of the drive sleeve 40. In view (b), the first turn of thread 31 on the lead screw 30 has a large pitch, and the other turns have a small pitch. During the first revolution, the lead screw 30 displacement depends on the large pitch of the first turn of thread 31 on the lead screw 30, so it displaces a large amount per revolution. For subsequent revolutions the lead screw 30 displacement depends on the smaller pitch of the lead screw thread 31, so it displaces a smaller amount. In view (c), the housing 10 thread 16 has a larger pitch than the lead screw 30. During the first revolution, the lead screw 30 displacement depends on the pitch of the housing thread 16, so it displaces a large amount per revolution. For subsequent revolutions the lead screw 30 displacement depends on the pitch of the lead screw thread 31, so it displaces a smaller amount.

REFERENCE NUMERALS

10 housing
11a, b opening
12 flange-like inner wall
13 strip
14 teeth
15 spline
16 inner thread
20 cartridge holder
30 lead screw (piston rod)
31 outer thread
32 clip arm
33 concave contact surface
40 driver (axially movable drive sleeve)
41 teeth
42 spline
43 ratchet teeth
44 threaded section
45 spline
46 last dose stop
47 ramp
50 nut
51 last dose stop
52 spline
60 dose indicator (number sleeve)
60a number sleeve lower
60b number sleeve upper
61 spline
62 flange
63 outer thread
64, 65 end stop
66 spline
67 clicker arm
68 groove
69 anchor point
70 button
71 stem
72 flange
73, 74 spline
75 ratchet teeth
80 dose selector
90 torsion spring
91, 92 hook
93, 94 coil
100 cartridge
101 bung
110 gauge element
111 helical feature
112, 113 stop
114 aperture
115, 116 flange
117 cam
118 recess
120 clutch plate
121 ratchet teeth
122 protrusion
123 clicker arm
130 clutch spring
140 bearing
141 disc
142 stem
143 convex contact surface
144 recessed portion
I longitudinal axis
R direction of revolution

The invention claimed is:

1. A drug delivery device to select and dispense a number of user variable doses of a medicament, the device comprising:
a housing;
a dose selector configured to set a dose by rotation relative to the housing;
a number sleeve arranged within the housing;
a first aperture in the housing, wherein at least a portion of the number sleeve is visible through the first aperture;
a drive sleeve;
a piston rod coupled to the housing and to the drive sleeve, wherein rotation of the drive sleeve relative to the housing causes the piston rod to translate relative to the housing;
a clutch mechanism releasably coupling the number sleeve and the drive sleeve, the clutch mechanism comprising:
a first interface configured to rotationally constrain the drive sleeve and the number sleeve depending on the axial position of the drive sleeve, and
a second interface configured to rotationally constrain the drive sleeve and the number sleeve via a clutch element depending on the axial position of the drive sleeve or the bias of a clutch spring; and
a drive spring, wherein relative rotation of the number sleeve and the drive sleeve during dose setting strains the drive spring and the drive spring is allowed to at least partially relax during dose dispensing thereby rotationally driving the number sleeve, the drive sleeve and the piston rod.

2. The drug delivery device according to claim 1, wherein the drive sleeve is axially movable between a first, proximal dose setting position and a second, distal dose dispensing position.

3. The drug delivery device according to claim 1, wherein the first interface comprises splines on an outer surface of the drive sleeve and corresponding splines on an inner surface of the number sleeve, wherein, in a first axial position of the drive sleeve relative to the housing or the number sleeve, the splines are engaged rotationally constraining the drive sleeve to the number sleeve, and wherein, in a second axial position of the drive sleeve relative to the housing or the number sleeve, the splines are disengaged allowing relative rotation of the drive sleeve and the number sleeve.

4. The drug delivery device according to claim 1, wherein the drive sleeve comprises a third interface configured to permanently rotationally constrain the drive sleeve and the piston rod.

5. The drug delivery device according to claim 1, wherein the drive sleeve comprises a fourth interface configured to rotationally constrain the drive sleeve and the housing depending on the axial position of the drive sleeve.

6. The drug delivery device according to claim 1, wherein the drive sleeve is coupled to a button via the clutch element, wherein, upon actuation of the button, the drive sleeve and the clutch element are translated against the bias of the clutch spring from a proximal position in which the drive sleeve is rotationally locked to the housing into a distal position in which the drive sleeve is rotationally un-locked from the housing, and wherein, upon release of the button, the clutch spring translates the drive sleeve, the clutch element and the button into the proximal position.

7. The drug delivery device according to claim 1, wherein the drive sleeve comprises a fifth interface configured to generate a feedback signal upon rotation of the drive sleeve and depending on the axial position of the drive sleeve.

8. The drug delivery device according to claim 1, further comprising a gauge element interposed between the housing and the number sleeve, wherein the gauge element has a second aperture positioned with respect to the first aperture of the housing, wherein at least a part of the number sleeve is visible through the first and second apertures (11*b*, 114), and wherein the gauge element (110) is axially guided within the housing (10) and in threaded engagement with the number sleeve (60) such that rotation of the number sleeve (60) causes an axial displacement of the gauge element (110).

9. The drug delivery device according to claim 1, further comprising at least one clicker arrangement configured to generate an audible or tactile feedback signal during dose setting, during dose dispensing or at the end of dose dispensing.

10. The drug delivery device according to claim 1, further comprising a button which is rotatable relative to the housing and rotationally locked to the number sleeve in a dose setting position and which is rotatable relative to the number sleeve and rotationally locked to the housing in a dose dispensing position.

11. The drug delivery device according to claim 1, further comprising a cartridge containing a medicament.

12. The drug delivery device of claim 11, wherein the medicament comprises a pharmaceutically active compound.

13. The drug delivery device of claim 1, wherein, during dose setting, the second interface is configured to prevent the number sleeve from rotating unless a torque applied to the second interface is greater than a torque applied by the drive spring on the number sleeve.

14. The drug delivery device according to claim 13, wherein the second interface comprises ratchet clutch features on the drive sleeve configured to engage corresponding ratchet clutch features on the clutch element which is rotationally permanently constrained to the number sleeve.

15. The drug delivery device according to claim 14, wherein each of the clutch features and the corresponding clutch features comprise teeth having a ramp angle allowing overhauling of each other for dose correction.

16. The drug delivery device according to claim 14, wherein the clutch spring is located axially interposed between the housing and the drive sleeve, wherein the clutch spring biases the drive sleeve towards the clutch element.

* * * * *